United States Patent [19]
Pienta

[11] Patent Number: 5,925,531
[45] Date of Patent: Jul. 20, 1999

[54] HUMAN BONE MARROW ENDOTHELIAL CELL LINE AND METHODS OF USE THEREOF

[75] Inventor: Kenneth J. Pienta, Ann Arbor, Mich.

[73] Assignee: The Regents of the University of Michigan, Ann Arbor, Mich.

[21] Appl. No.: 08/956,844

[22] Filed: Oct. 23, 1997

Related U.S. Application Data

[51] Int. Cl.$^6$ .............................. G01N 33/53; C12N 5/00
[52] U.S. Cl. ........................ 435/7.23; 435/378; 435/380; 435/373; 435/63; 435/64
[58] Field of Search ............................... 435/7.23, 240.2, 435/240.23, 378, 373, 380; 436/64, 63, 86

[56] References Cited

PUBLICATIONS

Galasko (1981) "Bone Metastases Studied in Experimental Animals," Clin. Orthop. 155:269–285.
Paget (1989) "Distribution of Secondary Growths in Cancer of the Breast," Lancet 1:571–573.
Galasko (1981) "The Anatomy and Pathways of Skeletal Metastases," in *Bone Metastasis,* Weiss and Gilbert, eds., G. K. Hall, Medical Publishers, pp. 49–63.
Jacobs (1983) "Spread of Prostatic Cancer to Bone," Urology 21:337–344.
Body (1992) "Metastatic Bone Disease: Clinical and Therapeutic Aspects," Bone 13:S57–S62.
Zetter et al. (1992) "The Cellular Basis for Prostate Cancer Metastasis," in *Prostate Cancer and Bone Metastasis,* J.P. Karr and H. Yamanaka, eds., Plenum Press, New York, pp. 39–43.
Bautista et al. (1990) "Insulin–like Growth Factors I and II are Present in the Skeletal Tissues of Ten Vertebrates," Metabolism 39:96–100.
Hauschka et al. (1986) "Growth Factors in Bone Matrix," J. Biol. Chem. 261:12665–12674.
Littlewood et al. (1991) "The Modulation of the Expression of IL–6 and Its Receptor in Human Osteoblasts in Vitro," Endocrinology 129:1513–1520.
Haq et al. (1992) "Rat Prostate Adenocarcinoma Cells Disseminate to Bone and Adhere Preferentially to Bone Marrow–derived Endothelial Cells," Cancer Res. 52:4613–4619.
Graham et al. (1973) "Transformation of Rat Cells by DNA of Human Adenovirus 5," Virology 54(2):536–539.
Pitot (1978) "The Language of Oncology," in *Fundamentals of Oncology,* marcel Dekker (Ed.), New York, pp. 15–28.
Rafii, et al. (1994) "Isolation and Characterization of Human Bone Marrow Microvascular Endothelial Cells: Hematopoietic Progenitor Cell Adhesion," Blood 84:10–19.
Schweitzer et al. (1995) "Isolation and culture of human bone marrow endothelial cells," Exp. Hematology 24:41–48.
Masek et al. (1994) "Isolation and culture of endothelial cells from huam bone marrow," Br. J. Haematol. 88:855–865.
Albelda et al. (1990) "Integrins and other cell adhesion molecules," FASEB J. 4:2868–2880.

Hynes (1992) "Integrins: Versatility, Modulation and Signaling in Cell Adhesion," Cell 69:11–25.
Oka et al. (1993) "Expression of E–Cadherin Cell Adhesion Molecules in Human Breast Cancer Tissues and its Relationship to Metastasis," Cancer Res. 53:1696–1701.
Honn et al. (1992) "Adhesion molecules and tumor cell interaction with endothelium and subendothelial matrix," Cancer and Metastasis Rev. 11:353–375.
Gamble et al. (1985) "Stimulation of the adherence of neutrophils to umbilical vein endothelium by human recombinant tumor necrosis factor," Proc. Nat. Acad. Sci. USA 82:8667–8671.
Sugama et al. (1992) "Thrombin–induced Expression of Endothelial P–Selectin and Intracellular Adhesion Molecule–1: A Mechanism for Stabilizing Neutrophil Adhesion," J. Cell. Bio. 119(4) 935–944.
Jackson et al. (1990) "Binding of human endothelium to *Ulex europaeus* I–coated Dynabeads: application to the isolation of microvascular endothelium," J. Cell Science 96:257–262.
Voyta et al. (1984) "Identification and Isolation of Endothelial Cells Based on Their Increased Uptake of Acetylated–Low Density Lipoprotein," J. Cell Bio. 99(6):2034–2040.
Montesano et al. (1983) "In Vitro Rapid Organization of Endothelial Cells into Capillary–like Networks Is Promoted by Collagen Matrices," J. Cell. Bio. 97:1648–1652.
Weibel et al. (1964) "New Cytoplasmic Components in Arterial Endothelia," J. Cell. Bio. 23:101–112.
Wagner et al. (1993) "The Weibel–Palade Body: the Storage Granule for von Willebrand Factor and P–selectin," Thromb. and Haemost. 70(1):105–110.
Piechocki et al. (1992) "TPA–induced differentiation of rat aortic endothelial cells is substrate–specific and receptor mediated," Exp. Sci. 61:152–157.
Inohara and Raz (1995) "Functional Evidence that Cell Surface Galectin–3 Mediates Homotypic Cell Adhesion," Cancer Res. 55:3267–3271.
Matsuno et al. (1994) "Inhibition of Integrin Function by a Cyclic RGD–Containing Peptide Prevents Neointima Formation," Circulation 90:2203–2206.
Almeida–Porada et al. (1996) "Isolation, characterization, and biologic features of bone marrow endothelial cells," J. Lab. Clin. Med. 128(4):399–407.
Schweitzer et al. (1997) "Characterization of a Newly Established Human Bone Marrow Endothelial Cell Line: Distinct Adhesive Properties for Hematopoietic Progenitors Compared with Human Umbilical Vein Endothelial Cells," Lab. Invest. 76(1)–25–36.
haq et al, Cancer Res. 52, 4613–4619, 1992.
Lotan et al, Glycoconjugate Journal, 11, 462–468, 1994.

*Primary Examiner*—Paula K. Hutzell
*Assistant Examiner*—Lin Sun-Hoffman
*Attorney, Agent, or Firm*—Medlen & Carroll, LLP

[57] ABSTRACT

The present invention provides immortalized human bone marrow endothelial cells which are useful for the study of tumor metastasis. In particular, the human bone marrow endothelial cell lines provided by the invention provide an in vitro model system for screening compounds for the ability to reduce, prevent, or inhibit the metastasis of cancer cells to bone tissue.

8 Claims, 4 Drawing Sheets

HUMAN BONE MARROW ENDOTHELIAL CELL LINE AND METHODS OF USE THEREOF

FIELD OF THE INVENTION

The present invention relates to immortalized human bone marrow endothelial cells. The present invention further relates to methods for using immortalized human bone marrow endothelial cell lines to study tumor metastasis and to screen compounds for the ability to reduce, prevent, or inhibit the metastasis of cancer cells to bone tissue.

BACKGROUND OF THE INVENTION

To date, cancer remains the single most common cause of morbidity and mortality of humans. The majority of cancer patients die as a result of metastasis of the primary tumor to tissues other than the primary tumor site, and in particular, to bone tissue. Patients with bone metastases have a poor prognosis which accounts for a large proportion of deaths resulting from cancer metastases. For example, in virtually 100% of patients with advanced disease, prostate cancer metastasizes to osseous sites and kills over 40,000 people per year.

Because the mechanisms which contribute to bone metastasis are poorly understood, rational drug design to reduce, prevent, or inhibit metastasis to bone has not been possible. It has been hypothesized that the bone environment provides a favorable growth advantage for cancer cells which non-selectively seed the bone marrow from the bloodstream (Galasko (1981) Clin. Orthop. 155:269–285; Paget (1989) Lancet 1:571–573; Galasko (1981) Bone Mestastes, Weiss and Gilbert, eds., G. K. Hall Medical Publisher, pp. 49–63; Jacobs (1983) Urology 21:337–344; Body (1992) Bone 13:S57–S62;). An alternative, but not mutually exclusive, hypothesis suggests that cancer cells preferentially bind to bone marrow endothelial cells as compared to endothelial cells lining the blood vessels of other organs. Once a tumor cell has successfully arrested in bone tissue, there are a myriad of growth factors and cytokines available that stimulate the cells to proliferate. Bone marrow contains many growth factors (e.g., transforming growth factor-beta, Insulin-like growth factors I and II, basic fibroblast growth factor, platelet-derived growth factor, interleukins-1and 6, and transferrin (Zetter et al. (1992) in *ProstateCancer and Bone Metastasis*, J. P. Karr and H Yamanaka, eds., Plenum Press, New York, N.Y.; Bautista et al. (1990) Metabolism 39:96–100; Hauschka et al. (1986) J. Biol. Chem. 261:12665–12674; Littlewood et al. (1991) Endocrinology 129:1513–1520;) which are normally involved in hemopoiesis and which have been shown to be powerful mitogens for a variety of cell lines. Indeed, cells from prostatic carcinoma appear to grow more rapidly in bone marrow than in the primary tumor (Zetter et al. (1992) in *ProstateCancer and Bone Metastasis*, J. P. Karr and H Yamanaka, eds., Plenum Press, New York, N.Y.).

The study of cancer metastasis to bone, and consequently, a rational approach to anti-metastatic drug design, have been hampered by the shortage of appropriate in vitro and in vivo models of tumor metastasis. To date, the principal prior art model for cancer metastasis to bone relies on injecting cancer cells into an animal, and observing seeding of cancer cells into bone tissue (see, e.g., (Haq et al. (1992) Cancer Res. 52:4613–4619). However, this in vivo model suffers from lack of reproducibility in seeding, as well as paucity of evidence on whether seeding was selective or non-selective (Haq et al. (1992) Cancer Res. 52:4613–4619).

Thus, there remains a need for a model for the study of tumor metastasis to bone.

SUMMARY OF THE INVENTION

The present invention provides immortalized human bone marrow cells which are useful in the study of tumor metastasis to bone, as well as in testing compounds for the ability to reduce, prevent, or inhibit tumor metastasis to bone.

More particularly, the invention provides a composition comprising an immortalized human bone marrow endothelial cell. While not intending to limit the invention's composition to any particular function or characteristic, in one preferred embodiment, the immortalized human bone marrow endothelial cell is capable of adhesion to a cancer cell. In a more preferred embodiment, the cancer cell is selected from the group consisting of prostate cancer cell, lung cancer cell, colon cancer cell, and breast cancer cell. In yet a more preferred embodiment, the cancer cell is a prostate cancer cell. In a particularly preferred embodiment, the prostate cancer cell is selected from the group consisting of LNCaP, DU-145, Pc-3M, and PC-3.

Also without intending to limit the immortalized human bone marrow endothelial cells to a particular characteristic, in one preferred embodiment, the adhesion of the cancer cell to the immortalized human bone marrow endothelial cell is greater than adhesion of the cancer cell to an endothelial cell selected from the group consisting of human umbilical vein endothelial cell, aortic endothelial cell, and microvascular endothelial cell.

Without restricting the immortalized human bone marrow endothelial cell to any specific composition, in one embodiment, the immortalized human bone marrow endothelial cell comprises a human bone marrow endothelial cell comprising a DNA sequence encoding SV40 large T antigen.

In an alternative preferred embodiment, the immortalized human bone marrow endothelial cell displays the same characteristics as the characteristics of HBME-1 cells.

Also provided by the present invention is an immortalized subclone of a composition comprising an immortalized human bone marrow endothelial cell.

The invention further provides a method of testing compounds, comprising: a) providing: i) one or more compounds to be tested; i) cancer cells; and ii) an immortalized human bone marrow endothelial cell capable of binding to the cancer cells; b) mixing, in any order: i) the compound; ii) the immortalized human bone marrow endothelial cell; and iii) the cancer cells; and c) detecting the extent of binding between the cancer cell and the immortalized human bone marrow endothelial cell.

While not intending to limit the cancer cell to any particular origin, in one embodiment, the cancer cell is selected from the group consisting of prostate cancer cell, lung cancer cell, colon cancer cell, and breast cancer cell. In one preferred embodiment, the cancer cell is a prostate cancer cell.

Also without limiting the type of compound used in the methods of the invention, in one embodiment, the compound is an antibody to a galectin. In an alternative embodiment, the compound is a polypeptide comprising the sequence Arg-Gly-Asp.

Also provided by the invention is a method of screening compounds for the ability to reduce, prevent or inhibit metastasis of a cancer cell to bone marrow tissue, comprising: a) providing: i) the cancer cell; and ii) an immortalized human bone marrow endothelial cell capable of adhesion to the cancer cell; b) contacting: i) the immortalized human bone marrow endothelial cell with the cancer cell under conditions such that the cancer cell adheres to the immortalized human bone marrow endothelial cell to form a cancer cell:bone marrow endothelial cell composition; and ii) the compound with the cancer cell:bone marrow endothelial cell composition to form a treated cancer cell:bone marrow endothelial cell composition; and c) detecting a reduction in adhesion between the cancer cell and the immortalized human bone marrow endothelial cell in the treated cancer cell:bone marrow endothelial cell composition compared to adhesion between the cancer cell and the immortalized human bone marrow endothelial cell in the cancer cell:bone marrow endothelial cell composition.

While not intending to limit the cancer cell to any particular origin, in one embodiment, the cancer cell is selected from the group consisting of prostate cancer cell, lung cancer cell, colon cancer cell, and breast cancer cell. In a preferred embodiment, the cancer cell is a prostate cancer cell.

BRIEF DESCRIPTION OF THE DRAWINGS

FIG. 1 shows endothelial cell characterization of the HBME-1 cell line.

DEFINITIONS

Figure 1A:
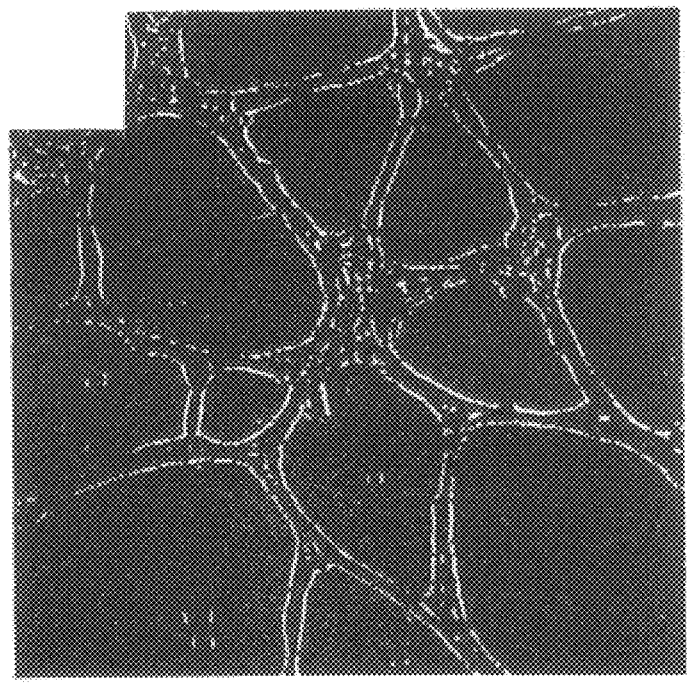
FIG. 1(a) is a micrograph showing tubule formation after 18 hour exposure to the extracellular matrix, Matrigel.

To facilitate understanding of the invention, a number of terms are defined below.

The terms "immortalized cell" and "cell line" when made in reference to a human bone marrow endothelial cell refer to one or more human bone marrow endothelial cells which are capable of a greater number of cell divisions in vitro as compared to the number of cell divisions by a primary human bone marrow endothelial cell or plurality of cells from which the immortalized cell is derived. An immortalized human bone marrow epithelial cell may be produced by several methods including the introduction of a "transgene" comprising nucleic acid (usually DNA) into a primary human bone marrow endothelial cell by way of human intervention, such as by the methods described herein. The number of cell divisions may be determined by the number of times a cell population may be passaged (i.e., subcultured) in in vitro culture. Passaging of cells is accomplished by methods known in the art. Briefly, a confluent or subconfluent population of cells which is adhered to a solid substrate (e.g., plastic Petri dish) is released from the substrate (e.g., by enzymatic digestion), and a proportion (e.g., 10%) of the released cells is seeded onto a fresh substrate. The cells are allowed to adhere to the substrate, and to proliferate in the presence of appropriate culture medium [e.g., Dulbecco's Modified Eagle Medium (DMEM; Gibco BRL), supplemented with 10% FBS, and 100 units/ml each of penicillin-streptomycin (Gibco BRL)]. The ability of adhered cells to proliferate may be determined visually by observing increased coverage of the solid substrate over a period of time by the adhered cells. Alternatively, proliferation of adhered cells may be determined by maintaining the initially adhered cells on the solid support over a period of time, removing and counting the adhered cells and observing an increase in the number of maintained adhered cells as compared to the number of initially adhered cells. Generally, though not necessarily, primary human bone marrow endothelial cells are capable of undergoing approximately eight passages in in vitro culture before cessation of proliferation and/or senescence. Thus, an immortalized human bone marrow endothelial cell which is derived from a primary human bone marrow endothelial cell that is capable of undergoing only 8 passages is a cell which is capable of at least 9 passages, preferably at least 12 passages, more preferably at least 17 passages, and most preferably at least 20 passages. An immortalized cell includes, but does not require, that the cell be capable of an infinite number of cell divisions.

A "transgenic human bone marrow endothelial cell" as used herein refers to a human bone marrow endothelial cell that includes a transgene which is inserted into, and which becomes integrated into, the genome of a primary human bone marrow endothelial cell. A "transgene" means a DNA sequence which is partly or entirely heterologous (i.e., not present in nature) to the cell in which it is found, or which is homologous to an endogenous sequence (i.e., a sequence that is found in the cell in nature) and is inserted into the cell's genome at a location which differs from that of the naturally occurring sequence. Transgenic human bone marrow endothelial cells which include one or more transgenes are within the scope of this invention.

The term "primary cell" when made in reference to a human bone marrow endothelial cell refers to a human bone marrow endothelial cell which is directly derived from bone tissue.

A "bone marrow endothelial cell" is a cell which is derived from bone tissue and which exhibits at least one endothelial cell marker or function. Endothelial cell markers are exemplified, but not limited to, (a) expression of the cell surface antigens: von Willibrand factor, UEA-I lectin, Beta-1, Alpha-5, CD11a, CD18, LFA-1, VLA-4, CD29, P-Selectin, E-Selectin, CD31, CD54, and vimentin, (b) the presence of increased uptake of acetylated-LDL as compared to epithelial cells and cancer cells, and (c) the presence of Weibel-Palade bodies as determined by electron microscopy. The presence of cell surface markers may be detected using methods known in the art and as described herein, including immunohistochemistry and flow cytometry (see, e.g., Example 2). Endothelial cell functions include, but are not limited to, formation of tubule structures when exposed to extracellular matrices as described herein (see, e.g., Example 2).

The term "subclone" as used herein refers to one or more cells which are derived from a "clone" of cells and which exhibit greater homogeneity with respect to at least one characteristic when compared to the clone from which the subclone is derived. A "clone" as used herein refers to a group of cells which is enriched for a population of genetically identical cells that are descended from a single common ancestor, as compared to a group of cells from which the clone was derived. Subclones may be obtained using routine methods in the art which generally, though not necessarily, rely on the use of serial dilution coupled with selection of cells exhibiting a desired characteristic. For example, where it is desirable to obtain from a clone of immortalized human bone marrow endothelial cells a subclone of immortalized human bone marrow endothelial cells which exhibit a greater level of binding to prostate cancer cells than the clone of immortalized human bone marrow epithelial cells, the following steps may be used. The clone of human bone marrow epithelial cells is serially diluted to obtain several subclones, and the subclones are tested for binding to the prostate cancer cells as described herein. The subclone which exhibits the highest binding to the prostate cancer cells relative to the other subclones is allowed to proliferate prior to further serial dilution and testing for binding. Sequential serial dilution, testing for the desired characteristic, and proliferation are repeated until a subclone is obtained which exhibits the desired level of enhanced binding to the cancer cells.

By the terms "capable of adhesion to a cancer cell" and "capable of binding to a cancer cell" when made in reference to a human bone marrow endothelial cell is meant that the human bone marrow epithelial cell is able to form and remain in physical contact with the cancer cell. The ability of a human bone marrow epithelial cell to adhere to a cancer cell may be determined by methods described herein. Briefly, the cancer cell is labelled with a $^{51}$Cr salt, placed in suspension, added to confluent cultures of human bone marrow endothelial cells and allowed to adhere for 30 minutes. Floating cells are then washed off and the amount of radioactivity in each fraction is determined. The detection of an amount of radioactivity which is greater than, preferably at least two-fold greater than, more preferably at least three-fold greater than, and most preferably at least four-fold greater than, the amount of radioactivity in a control sample (e.g., a sample containing a mixture of normal cells and human bone marrow endothelial cells) indicates that the human bone marrow endothelial cells are capable of adhesion to the cancer cells.

The term "specific adhesion to a cancer cell" when made in reference to a human bone marrow endothelial cell refers to the preferential binding between a human bone marrow endothelial cell to the cancer cell as compared to the binding between an endothelial cell from other than human bone marrow (e.g., from microvascular or aortic tissue) to the cancer cell. The level of binding of the human bone marrow endothelial cell to the cancer cell is preferably at least two-fold greater than, more preferably at least three-fold greater than, and most preferably at least four-fold greater than, the level of binding of an endothelial cell from other than human bone marrow to the cancer cell.

The term "transfection" as used herein refers to the introduction of a transgene into a cell. The term "transgene" as used herein refers to any nucleic acid sequence which is introduced into the genome of a cell by experimental manipulations. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, biolistics (i.e., particle bombardment) and the like. Transfection may be stable or transient. The term "stable transfection" or "stably transfected" refers to the introduction and integration of a transgene into the genome of the transfected cell. The term "stable transfectant" refers to a cell which has stably integrated one or more transgenes into the genomic DNA. The term "transient transfection" or "transiently transfected" refers to the introduction of one or more transgenes into a transfected cell in the absence of integration of the transgene into the host cell's genome. The term "transient transfectant" refers to a cell which has transiently integrated one or more transgenes.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of ribonucleotides along the mRNA chain, and also determines the order of amino acids along the polypeptide (protein) chain. The DNA sequence thus codes for the RNA sequence and for the amino acid sequence.

The term "SV40 large T antigen" as used herein refers to the amino acid sequence encoded by the large T-SV40 genome as previously described (Graham et al. (1973) Virology 54(2):536–539).

The term "display same characteristics as the characteristics of HBME-1 cells" when used in reference to a cell refers to a cell which displays the following combination of characteristics: (a) ability to be passaged beyond at least nine passages, (b) positive staining, as detected by immunohistochemistry and/or flow cytometry, for endothelial cell markers (e.g., von Wilibrand factor), integrins (e.g., beta-1, Alpha-5, CD11a, CD18, LFA-1, VLA-4, CD29), selectins (e.g., P-Selectin and E-Selectin), and other endothelial cell antigens (e.g., CD31, CD54, UEA-I lectin, and Vimentin), (c) increased uptake of acetylated-LDL as compared to epithelial cells or cancer cells, (d) and presence of Weibel-Palade bodies as detected by electron microscopy, (e) rapid (i.e., within 24 hours) formation of tubule structures when exposed to extracellular matrices, (f) preferential adhesion to prostate cancer cells compared to adhesion of endothelium derived from aortic endothelial cells or from microvascular endothelial cells to prostate cancer cells.

The terms "cancer cell" and "tumor cell" refer to a cell undergoing early, intermediate or advanced stages of multi-step neoplastic progression as previously described [H. C. Pitot (1978) in "Fundamentals of Oncology," marcel Dekker (Ed.), New York pp 15–28]. The features of early, intermediate and advanced stages of neoplastic progression have been described using microscopy. Cancer cells at each of the three stages of neoplastic progression generally have abnormal karyotypes, including translocations, inversion, deletions, isochromosomes, monosomies, and extra chromosomes. A cell in the early stages of malignant progression is referred to as "hyperplastic cell" and is characterized by dividing without control and/or at a greater rate than a normal cell of the same cell type in the same tissue. Proliferation may be slow or rapid but continues unabated. A cell in the intermediate stages of neoplastic progression is referred to as a "dysplastic cell." A dysplastic cell resembles an immature epithelial cell, is generally spatially disorganized within the tissue and loses its specialized structures and functions. During the intermediate stages of neoplastic progressions an increasing percentage of the epithelium becomes composed of dysplastic cells. "Hyperplastic" and "dysplastic" cells are referred to as "pre-neoplastic" cells. In the advanced stages of neoplastic progression a dysplastic cell become a "neoplastic" cell. Neoplastic cells are typically invasive i.e., they either invade adjacent tissues, or are shed from the primary site and circulate through the blood and lymph to other locations in the body where they initiate secondary cancers. The term "cancer" or "neoplasia" refers to a plurality of cancer cells.

The term "metastasis" as used herein refers to the processes by which a cancer cell is translocated from a primary cancer site (i.e., a location where the cancer cell initially formed from a normal, hyperplastic or dysplastic cell) to a site other than the primary site, where the translocated cell lodges and proliferates. A number of hypotheses have been proposed for metastasis of cancer cells to bone. The "seed and soil" description of tumor metastasis suggested by Stephen Paget over 100 years ago has been supported by abundant experimental evidence (Paget (1989) Lancet 1:571–573). In essence, invading tumor cells will arrest and grow where the environment is the most agreeable. An alternative theory is that there are specific receptor/ligand complexes established between circulating tumor cells and the endothelium of bone tissue. These theories are not mutually exclusive and the actual mechanism may be a combination of both.

The terms "reduction in adhesion" and "reduction in binding" when made in reference to a reduction in adhesion between a cancer cell and a treated immortalized human bone marrow endothelial cell as compared to adhesion between the cancer cell and an untreated immortalized human bone marrow endothelial cell" as used herein refers to a quantity of cancer cells which is bound to treated immortalized human bone marrow endothelial cells, wherein this quantity is less than, preferably at least 10% less than, more preferably at least 25% less than, yet more preferably at least 30% less than, and most preferably is the same as, the quantity of cancer cells which are bound to untreated immortalized human bone marrow endothelial cells, as detected by the methods described herein. When the same quantity of binding of a cancer cell to an untreated immortalized human bone marrow endothelial cell is measured, this may indicate that adhesion between the cancer cell and the treated immortalized human bone marrow endothelial cell is completely inhibited. A reduced level of adhesion need not, although it may, mean an absolute absence of adhesion. The invention does not require, and is not limited to, compounds which eliminate adhesion of cancer cells to treated immortalized human bone marrow endothelial cells.

The term "detecting the extent of adhesion" and "detecting the extent of binding" when made in reference to adhesion of a cancer cell and an immortalized human bone marrow endothelial cell refers to measuring a quantity of binding between the cancer cell and the immortalized human bone marrow cell. Such measurement may be accomplished using methods described herein (see, e.g., Example 3, and FIG. 2).

DESCRIPTION OF THE INVENTION

The present invention provides immortalized human bone marrow endothelial cells which are useful in the study of tumor metastasis. Also provided by the invention are methods for using the immortalized human bone marrow endothelial cells to screen compounds for the ability to reduce, prevent or inhibit the metastasis of cancer cells to bone tissue. The description of the invention is divided into (A) Immortalized Human Bone Marrow Endothelial Cells, and (B) Methods Of Screening Anti-Metastatic Compounds.

A. Immortalized Human Bone Marrow Endothelial Cells

The present invention provides a cell line of human bone marrow endothelial cells. In one preferred embodiment, the human bone marrow endothelial cell line is generated by transfecting endothelial cells obtained from the posterior iliac crest of a normal young male with an expression plasmid which contains a DNA sequence encoding SV40 late T-antigen.

However, the cell lines of the invention are contemplated not to be restricted to the origin of the cells used for transfection. Any endothelial cell derived from any osseous structure in the human body is contemplated to be within the scope of this invention. Methods for isolating human bone marrow endothelial cells have been previously described (Rafii et al. (1994) Blood 84:10–19; Schweitzer et al. (1995) Exp. Hematology 24:41–48; Masek et al. (1994) Br. J. Haematol. 88:855–865) and are exemplified by the method described herein. The endothelial nature of cells isolated from human bone marrow may be readily determined by the detection of specific endothelial markers (e.g., Factor VIII, UEA-I lectin, vimentin, etc.) using commercially available antibodies.

It is also contemplated that transfection of primary human bone marrow endothelial cells is not limited to the plasmid used herein. Any vector (e.g., including retrovirus, plasmids, etc.) which is capable of stably transfecting a DNA sequence encoding the SV40 late-T antigen is contemplated to be within the scape of the invention.

The immortalized human bone marrow endothelial cells of the invention were characterized by exhibiting, among other characteristics, positive staining for von Willibrand factor, binding of UEA-1 lectin, increased uptake of acetylated-LDL, presence of Weibel-Palade bodies, and rapid formation of tubule structures when exposed to extracellular matrices. Interestingly, in an in vitro assay, cancer cells (particularly prostate cancer cells) adhered preferentially to the immortalized human bone marrow endothelium as compared to endothelium derived from other sources. This preferential adhesion was at least partially dependent on magnesium and calcium ions and was blocked, in part, by antibodies to galactin-3. Data presented herein demonstrates that the human bone marrow endothelial cell lines of the invention are useful for the study of processes underlying metastasis as well as for screening compounds capable of reducing, preventing, or inhibiting metastasis of cancer cells to bone tissue, as described below.

B. Methods Of Screening Anti-Bone Metastatic Compounds

The invention provides methods for screening anti-metastatic compounds which reduce, prevent or inhibit cancer metastasis to bone tissue. These methods rely on the use of the immortalized human bone marrow endothelial cell lines provided herein. The methods of the invention exploit the novel characteristic that tumor cells preferentially bind to the invention's cell lines as compared to binding to endothelial cells from other than bone marrow. Screening of a compound for its ability to reduce, inhibit, or prevent bone metastasis of a cancer of interest relies on observing a reduction in adhesion of cells of the cancer of interest to the human bone marrow endothelial cell lines of the invention. Treatment of the cancer cells alone, the cell lines of the invention alone, with the tested compound may be performed prior to contacting the cancer cells and cell lines of the invention under conditions which allow adhesion of the cancer cells to the cell lines. Alternatively, treatment with the tested compound may be performed simultaneously or subsequent to contacting the cancer cells and cell lines of the invention under conditions which allow adhesion of the cancer cells to the cell lines.

While not limited to any particular mechanism, data presented herein suggests that there is a specific receptor-:ligand interaction which mediates both the "docking" and "locking" of cancer cells to bone marrow endothelial cells.

Cell adhesion molecules such as cadherins, selectins and integrins may be important mediators of tumor cell/bone associations and many cell adhesion molecules in tumor cells are upregulated by cytokines present in bone marrow (Albelda et al. (1990) FASEB J. 4:2868–2880; Haynes (1992) Cell 69:11–25; Oka et al. (1993) Cancer Res. 53:1696–1701). It has been suggested that the interaction of a circulating tumor cell with the endothelium involves two distinct steps, an initial "docking" step which may be mediated by lectin-carbohydrate interactions and a second "locking" step which is mediated by integrins (Honn et al. (1992) Cancer and Metastasis Rev. 11:353–375).

Without limiting the invention to a particular theory, adhesion data presented herein suggests that lectin-carbohydrate interactions are important because a polyclonal antibody to galactin-3 inhibits prostate cancer cell-binding to HBME-1 by more than 50%. In addition, the galactose containing molecule modified citrus pectin inhibits binding in a concentration dependent manner.

Also without intending to restrict the invention to a particular hypothesis, additional adhesion data disclosed herein further suggests that integrin interactions may be important in binding because RGD peptide inhibited binding of PC-3 cells to HBME-1 cells.

Without intending to limit the invention to any particular mechanism, it is the inventor's consideration that the inability of any particular antibody or agent to inhibit adhesion completely may be due to the presence of more than one population of cells with different adherence ability within the general population of endothelial cells. This mechanism may be further investigated by isolating subclones of the immortalized human bone marrow endothelial cells which contain specific populations of endothelial cells that exhibit a more homogenous level of adherence to a particular cancer cell as compared to the level of adherence of the HBME-1 cells to the same cancer cell. Another explanation for variable adhesion is that the cancer cells used in these experiments may be heterogenous and have different amounts of expression of important cell surface markers. A third potential explanation for difference in inhibition lies in the use of commercial antibodies which may or may not be blocking antibodies in the methods used herein.

Experimental

The following examples serve to illustrate certain embodiments and aspects of the present invention and are not to be construed as limiting the scope thereof.

EXAMPLE 1

Isolation And Immortalization of Bone Marrow Endothelial Cells

In order to generate a bone marrow endothelial cell line, primary bone marrow endothelial cells were isolated from a 25 year old Caucasian man and characterized for their endothelial character as described below. The mortal endothelial cells were then immortalized with SV-40 large-T antigen to create a cell line as described below.

A. Isolation of Primary Bone Marrow Endothelial Cells

Bone marrow aspirates were obtained from the posterior iliac crest of a normal 25 year old white male volunteer donor. Five mL of the aspirate was immediately combined with 0.1 ml of a 34 mM EDTA solution to prevent coagulation of the specimen. The aspirate was placed on ice and maintained at 4° C. for the duration of the isolation procedure. After freezing 1 ml of the aspirate in fetal bovine serum (FBS; Gibco BRL. Gaithersburg, Md.)/5% dimethylsulfoxide for further study, the remaining aspirate was washed twice with 50 ml Hanks' balanced salt solution without $Ca^{++}$ or $Mg^{++}$ salts (HBSS; Gibco BRL) to remove insoluble lipids. The remaining pellet was suspended in 20 ml HBSS, 3 ml aliquots of the suspension were carefully layered over 3 mls of Ficoll-Hypaque (Sigma, St. Louis, Mo.) density gradients (d=1.077 $g/cm^3$) and centrifuged at 400×g for 30 minutes to isolate the mono-nucleated cells (MNCs). The procedure was repeated to ensure low numbers of contaminating erythrocytes or platelets. Any remaining Ficoll was removed by washing the pellet twice with 50 ml HBSS.

The pellet was resuspended in minimal essential media (MEM; Gibco BRL) containing 1.0% (w/v) bovine serum albumin (Sigma) to inhibit formation of aggregates. Cells were then incubated with 50 ng/ml of tumor necrosis factor-alpha (TNF-alpha; Collaborative biomedical Products Bedford, Mass.) for 4 hours to promote expression of adhesion molecules (Gamble et al. (1985) Proc. Nat. Acad. Sci. USA 82:8667–8671). Lectin P-selectin was the target antigen that was used to differentiate endothelium in the bone marrow from other MNCs as previously described (Sugama et al. (1992) J. Cell Bio. 119(4) 935–944). After the upregulation of adhesion antigens with the cytokine, the cells were incubated with a fluorescein labeled monoclonal anti-human P-selectin antibody (Endogen, Inc., Cambridge, Mass.) at a concentration of 10 ug/ml for 1 hour. P-selectin positive cells were sorted from other MNCs using an Epics Elite Fluorescence Activated Cell Sorter (FACS; Coulter Electronics, Haileah, Fla.) equipped with an argon laser to excite the fluorescein in the 488 nM range. The brightest 1.0% of the cells were directed into a 96-well plate at concentrations ranging from 1 to 1000 cells/well. Positive, sorted cells were maintained in 96-well plates in Dulbecco's Modified Eagle Medium (DMEM; Gibco BRL), supplemented with 10% FBS, and 100 units/ml each of penicillin-streptomycin (Gibco BRL). To confirm their endothelial nature, the isolated were characterized by as described below.

B. Immortalization of Isolated Primary Bone Marrow Endothelial Cells

Primary bone marrow endothelial cells proliferating in the 96-well plates were transferred to 100 mm tissue culture dishes for transfection with the pMT10D plasmid containing the large T-SV40 genome (Graham et al. (1973) Virology 54(2):536–539). Briefly, 30 ug of plasmid was introduced into each 100 mm culture dishes of bone endothelium utilizing the $CaPO_4$ method of DNA transfection with the Mammalian transfection kit (Stratagene, La Jolla, Calif.) (Honn et al. (1992) Cancer and Metastasis Rev. 11:353–375). After 24 hours, the cells were washed twice with HBSS and incubated in reduced serum (5.0%) media to promote growth of transfected cells while limiting that of non-transfected cells. Cells were frozen for future use at early passages.

Karyotyping of passage four of the SV40-transfected bone marrow endothelial cells (hereinafter referred to as HBME-1 cells or HBME-1 cell line) revealed a heterogeneous karyotype with both diploid and hyper-tetraploid populations of cells. Unless otherwise mentioned, immortalized cells in the following experiments were utilized at passage eight.

EXAMPLE 2

Characterization of Immortalized Bone Marrow Endothelial Cells

Consistent with their origin from the fenestrated sinusoidal endothelium of the bone, the HBME-1 cells displayed an endothelial-like morphology and had a doubling time of 33 hours. The HBMF-1 cell line also displayed the characteristic of contact-mediated inhibition of growth once confluence in tissue culture was observed, and had the tendency to slough in sheets when agitated as if to mimic the barrier nature of endothelium in vivo. The cells were easily harvested from tissue culture by trypsinization and grow well in standard DMEM supplemented with 10% FBS.

In contrast to primary bone marrow endothelial cells which could not be passaged beyond approximately eight passages, the SV40-transfected bone marrow endothelial cells were capable of undergoing at least 20 passages over approximately eighteen months. Also in contrast to primary bone marrow endothelial cells, the SV40-transfected bone marrow endothelial cells continued to proliferate in a reduced serum concentration (5% fetal calf serum) as compared to the serum concentration (10% fetal calf serum) required to maintain proliferation of the primary bone marrow endothelial cells.

Endothelial cells can be positively identified through a variety of specific markers (e.g., the presence of the cell surface antigens P-selectin, E-selectin, vimentin, $\beta_1$-integrin, $\alpha_5$-integrin, and the presence of Weibel-Palade bodies) and functions (e.g., increased uptake of acetylated low density lipoprotein, and tubule formation on extracellular matrix. In order to ascertain the endothelial nature of the HBME-1 cells, the following experiments were conducted.

A. Immunohistochemistry

Bone endothelium was seeded in 4-well chamber slides (Nunc, Inc., Naperville, Ill.) at a concentration of $1 \times 10^5$ cells/well. After 48 hours the cells were washed once with phosphate buffered saline (PBS) and incubated with methanol at $-20°$ C. After 20 minutes, the cells were washed twice with PBS and incubated in 3.7% ice-cold formaldehyde for 10 minutes followed by 3×1 minute PBS washes. To block non-specific binding, cells were incubated in 1.0% mouse or rabbit serum/PBS (depending on which host raised the primary antibody) for 30 minutes at room temperature. After blocking, the cells were again washed 3×1 minute with PBS. Bone endothelial cells were incubated with the following primary antibodies: anti-Beta-1 (Gibco BRL), anti-Alpha-5 integrin (Gibco BRL), anti-Factor VIII (Dako, Carpinteria, Calif.), anti-CD31 (Dako), anti-CD29 (Dako), anti-P-selectin (R & D Systems, Minneapolis, Minn.), anti-E-selecting (R & D Systems), L-selectins (R & D Systems), anti-VCAM-1 (R & D Systems), anti-ICAM-1 (R & D Systems), anti-ICAM-2 (R & D Systems), anti-ICAM-3 (R & D Systems), anti-CD11a (R & D Systems), anti-CD18 (R & D Systems), CD44 (Sigma), Vimentin (Sigma), pan-cytokeratin (Sigma), LFA-1 (Sera Lab, Sussex, UK), VLA-4 (Seikagaku America, Inc., Rockville, Md.). The antibodies were used at concentrations ranging from 2–20 ug/ml for 1 hour at 25° C. Cells were washed 5×1 minute with PBS and incubated with mouse or rabbit anti-human secondary antibodies conjugated with Fluorescein (FITC; Sigma) at concentrations recommended by the manufacturer. Alternatively, the cells were incubated with 10 ug/ml FITC conjugated UEA-1 lectin (Sigma), which has been reported to bind specifically to human endothelium, for 1 hour at room temperature (Jackson et al. (1990) J. Cell Science 96:257–262). Negative controls were cells incubated with secondary antibodies only. The stained cells were visualized utilizing the singlepass filter on a Zeiss Axioscope fluorescence microscope. After washing in 2×PBS, the cells were covered in 80%glycerol/20%PBS and visualized under fluorescence microscopy. Staining by immunohistochemistry was reported as positive (+) or negative (−) by two independent reviewers and recorded as Table 1. Where staining was positive, the number of cells which were stained relative to the total number of cells in each assay was recorded.

TABLE 1

| Antigen | Immunohistochemistry | Flow Cytometry % positive |
|---|---|---|
| Integrin family | | |
| Beta-1 | + | + (99%) |
| Alpha-5 | + | + (99%) |
| CD11a | + | + (5%) |
| CD18 | + | + (20%) |
| LFA-1 | + | na[1] |
| VLA-4 | + | na |
| CD29 | + | + (99%) |
| Selectin family | | |
| P-Selectin | + | + (50%) |
| E-Selectin | + | + (50%) |
| L-Selectin | − | − |
| IgG family/other markers | | |
| CD31 (PECAM) | + | + (3%) |
| CD106 (VCAM-1) | + | − |
| CD54 (ICAM-1) | + | + (15%) |
| CD102 (ICAM-2) | − | − |
| CD50 (ICAM-3) | − | − |
| CD44 (HCAM) | na | + (44%) |
| Vimentin | + | + (50%) |
| pan-Cytokeratin | − | na |

[1]na: Not available
Essentially the same results as those shown above in Table 1 were also obtained when HBME-1 cells in the eighteenth passage were used.

B. Flow Cytometry

Mean fluorescence was reported by flow cytometry as follows. Cells in culture were harvested by trypsinization. For each marker, $2 \times 10^6$ cells were suspended in 0.5 ml PBS containing 1.0% FBS. Primary antibodies were added at concentrations of 10 ug/ml and incubated at 4° C. for 30 minutes. The cells were washed 3 times with ice cold PBS containing 0.1% sodium azide, and incubated with anti-mouse or anti-rabbit secondary antibodies for 30 minutes at 4° C. The cells were washed 3 times with PBS-NaN$_3$ followed by incubation in 2.0% paraformaldehyde, pH 7.4 for 5 minutes. The cells were washed 3 times with PBS and analyzed for fluorescence with an Epics XL flow cytometer (Coulter Corp., Hialeah, Fla.).

C. Low Density Lipoprotein (LDL) Uptake Analysis

Isolated HBME-1 cells were analyzed to asses their ability to uptake acetylated-low density lipoprotein (Voyta et al. (1984) J. Cell Bio. 99(6):2034–2040). Briefly, cells growing on chamber slides were incubated with 10 ug/ml DiI-Ac-LDL (Biomedical Technologies, Stoughton, Mass.) for 4 hours at 37° C. The cells were washed 3 times with HBSS, and fixed in 3.7% formaldehyde. Qualitative results were visualized using standard rhodamine excitation on the triplepass Zeiss axioscope filter. Alternatively, cells were similarly prepared for quantitative analysis utilizing flow cytometry.

D. Tubule Formation

Bone marrow endothelium rapidly will organize into capillary-like networks when grown on the extracellular matrix Matrigel (Montesano et al. (1983) J. Cell.Bio. 97:1648–1652). 100 uL of Matrigel (Collaborative Biomedical Prod.) was carefully layered over the surface of each chamber in a four chamber tissue culture slide. Endothelial cells were added at different concentrations ranging from $2 \times 10^5$–$2 \times 10^6$ cells/well. Tubule structures were photographed 18 hours later using a standard light microscope.

E. Electron Microscopy

Electron micrographs of the bone marrow endothelial cells were obtained for ultrastructural analysis. Specifically, cells were examined for the presence of Weibel-Palade bodies, which are endothelial-specific membrane-bound organelles that are considered to be storage granules for von Willebrand factor and other antigens (Weibel et al. (1964) J. Cell. Bio. 23:101–112; Wagner et al. (1993) Thromb and Haemost. 70(1):105–110). Micrographs were taken after cells were fixed in 2.5% glutaraldehyde overnight at 4° C., incubated in buffered osmium tetroxide for one hour, dehydrated in ethanol, embedded in epoxy resin, thin sectioned, double stained, and examined with a Phillips CM-100 transmission electron microscope.

F. Results

Figure 1B:
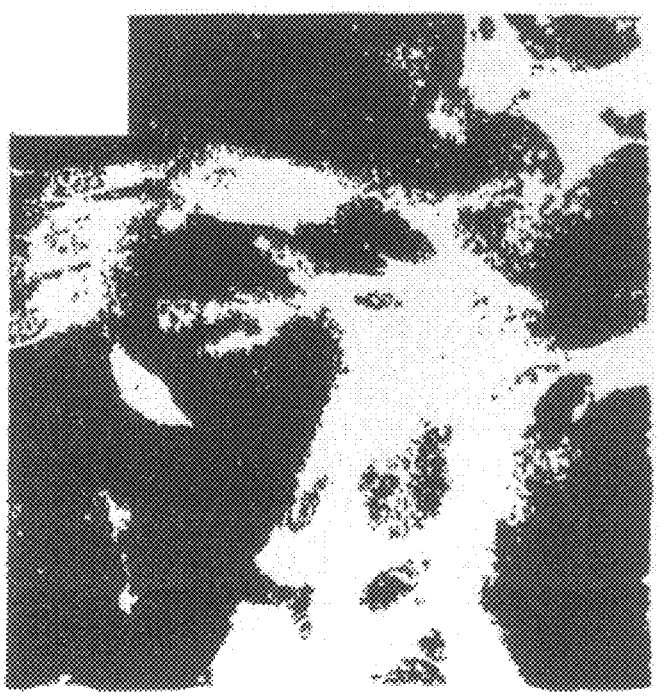
FIG. 1(b) is an immunohistochemical analysis showing positive staining of immortalized HBME-1 cells for von Willebrand factor; negative control (i.e., in the absence of von Willebrand factor antibody) is in the right corner; Bar represents 10 μm.

HMBE-1 rapidly (i.e., within 24 hours) formed tubule structures when plated on Matrigel (FIG. 1a). HMBE-1 cells demonstrated positive staining for von Willebrand factor (FIG. 1b) and many other endothelial specific antigens, integrins and selectins (Table 1). These observations confirm the endothelial nature of the HBME-1 cells. In addition, the fact that a similar profile of endothelial marker staining was observed with HBME-1 cells at the fourth and eighteenth passages (Table 1) demonstrates stable expression of these markers in HBME-1 cells.

Figure 1C:
FIG. 1(c) is an electron micrograph showing the presence of Weibel-palade bodies (arrow) in the cytoplasm of the HBME-1 cell line; Bar represents 200 nm.
Figure 1D:
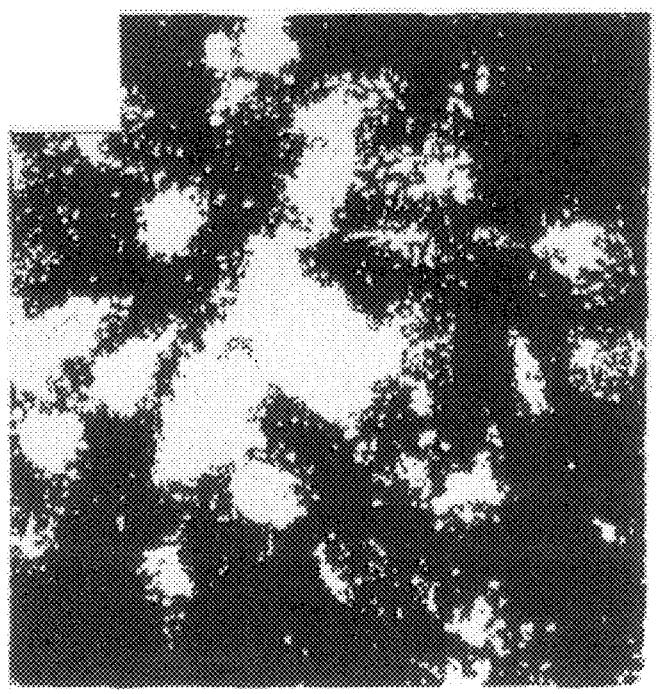
FIG. 1(d) is a light micrograph showing increased uptake of acetylated-LDL by the HBME-1 cell line; negative control is shown in the right corner; Bar represents 10 μm.

In addition, Weibel-Palade bodies, the storage granules for Factor VIII, were demonstrated by electron microscopy (FIG. 1c) HBME-1 cells also displayed increased uptake of acetylated low density lipoprotein as compared to epithelial cells or cancer cells (FIG. 1d). Positive binding of the endothelial cell specific lectin UEA-I by HMBE-1 cells was also demonstrated (data not shown). These results further confirmed the endothelial nature of the HBME-1 cells.

EXAMPLE 3

Adhesion of Immortalized Bone Marrow Endothelial Cells to Cancer Cells

In order to determine whether the HBME-1 cells were capable of adhesion to cancer cells, HBME-1 cells were incubated with cancer cell lines derived from several tissues [human prostate cancer cell lines: TSU, DU-145, PC-3, LNCaP and PC-3M; a novel cell line derived from a metastatic spinal lesion: Spine Met; breast cancer cell line: MCF-7; lung tumor cell line: SK-MES-1, and colon tumor cell line: WiDr], as well as with nonmalignant epithelial cell lines [nonmalignant prostate epithelial cell line: PrEC-1; and nonmalignant breast epithelial cell line: MCF-10a]. The number of cancer cells which adhered to the HBME-1 cells was estimated as follows.

A. Cell Lines and Cell Culture

The InCaP, DU-145, PC-3, WiDr, MCF-7, HUVEC, and SK-MES-1 cell lines were all obtained from the American Type Culture Collection (ATCC), (Rockville, Md.). PC-3M was a gift of Dr. Stearns, Medical College of Pennsylvania, Philadelphia, Pa. TSU was a gift of Dr. John Isaacs, Johns Hopkins School of Medicine, Baltimore, Md. PrEC-1 was a gift of Dr. Mark Day, University of Michigan Comprehensive Cancer Center, Ann Arbor, Mich. MCF10a was a gift of the late Dr. Herb Soule, Michigan Cancer Foundation, Detroit, Mich. The spinal met is a prostate cancer cell line derived from the spine of a patient with hormone refractory prostate cancer developed in our laboratory.

Culture media and components were purchased from Sigma. LNCaP, PC-3, PrEC-1, the spinal met and PC3M were maintained in 89% RPMI, 10% fetal bovine serum (FBS) and 1% penicillin/streptomycin. DU-145, HUVEC, SK-MES-1, WiDr and MCF-7 were maintained in 89% Eagle's MEM, 10% fetal bovine serum (FBS) and 1% penicillin/streptomycin. MCF10a was maintained in a 1:1 mixture of Dulbecco's modified Eagle's medium and Ham's F12 medium with 20 ng/ml epidermal growth factor, 100 ng/ml cholera toxin, 0.01 mg/ml insulin, and 500 ng/ml hydrocortisone, 95% and 5% horse serum.

B. Adhesion Assay

The ability of tumor cells to adhere to HBME-1 cells was determined as follows. $1.2 \times 10^6$ PC-3 cells were harvested from tissue culture and incubated in 5.0 mls MEM with 1.0% BSA and 10 $uCi^{51}$ Cr sodium salt (NEN- Dupont, Boston, Mass.) for 1 hour at 37° C. The cells were washed three times in isotope free media and $1 \times 10^5$ radioactively labeled tumor cells were layered in quadruplicate over monolayers of endothelium growing in 'snap-apart' 96 well tissue culture plates (Costar/Fisher Scientific) and incubated for 30 minutes at 37° C. The plates were gently washed 3×with PBS, and the resulting endothelial/tumor cell combination was assayed for radioactivity by disassembling the plates and checking each well for gamma particle emission using a TmAnalytic GammaTrac 1191 gamma counter. Adhesion was calculated as % Adhesion=Bound cpm/Total cpm×100%. Adhesion is reported as relative counts per minute as compared to control human umbilical vein endothelium cells (HUVECs), which have been set to equal 100 across all experiments. Adhesion was assayed in quadruplicate and the experiments were repeated three times.

Figure 2:
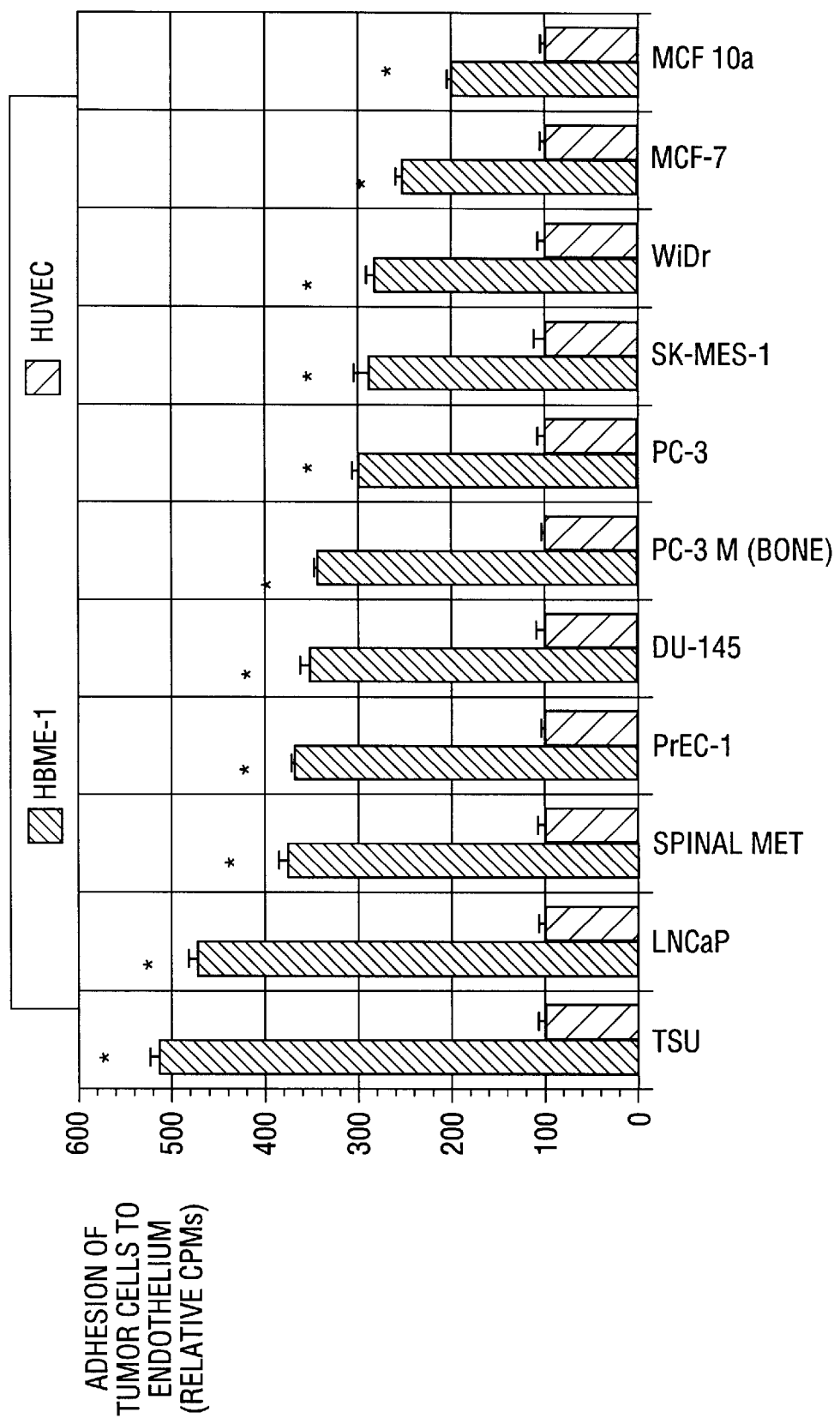
FIG. 2 is a graph showing adhesion of tumor cells to HBME-1 and to HUVEC endothelial cells. Bars represent standard error (* p<0.01).

The results of the adhesion assay are shown in FIG. 2. All cancer cell lines derived form various tissues (prostate, lung, colon and breast) preferentially adhered to the HBME-1 cells as compared to HUVECs. In particular, human prostate cancer cell lines showed the highest such preferential adhesion; the human prostate cancer cell lines PC-3, PC-3M (a daughter cell line derived from a bone metastasis), LNCaP, TSU PrEC-1, and DU-145 all demonstrated a higher preferential adhesion to HMBE-1 cells as compared to HUVECs (FIG. 2, greater than three fold increase in adhesion). The breast cancer cell line MCF-7, the immortal breast epithelial cell line MCF10a, the colon cancer cell line WiDr and the lung cancer cell line SK-MES-1 also adhered preferentially to the bone marrow endothelium (2–2.5 fold). Similar results were obtained when the HBME-1 cells were compared to aortic endothelial cells and microvascular endothelial cells derived from lung capillaries (Gift of Dr. Jim Onada, Waynes State University, Detroit, Mich.; Piechacki et al., (1992) Exp. Sci. 61:152–157) (data not shown).

EXAMPLE 4

Inhibition of Adhesion of Bone Marrow Endothelial Cells to Cancer Cells

Agents which suppress adhesion of prostate tumor cells to bone marrow endothelial cells could either interfere with the initial docking (thought to be lectin mediated) of the cancer cell to the endothelial cell or the secondary locking of the cell (thought to be integrin mediated) (18). In order to determine whether HBME-1 cells could be used to ascertain the effect of a test agent on adhesion of cancer cells to bone, the effect of a number of agents on inhibition of PC-3 adhesion to HBME-1 was assessed as follows.

In order to investigate whether carbohydrate residues mediate adhesion of cancer cells to bone, the effect of the citrus pectin carbohydrate molecule and of an antibody to galectin-3 on adhesion of PC-3 prostate cancer cells to HBME-1 cells was determined. Similarly, to investigate whether integrin interactions were important in maintaining adhesion between the docked tumor cells and the HBME-1 cells, the effect of treatment with anti-integrin antibodies and treatment with peptides containing RGD sequences on binding of PC-3 to HMBE-1 was investigated. Monolayers of HBME-1 were incubated for 30 minutes with potential anti-adhesive substances, including 0.1% modified citrus pectin (MCP: a polygalacturonic acid polymer), polyclonal antibody to galectin-3, the following monoclonal antibodies: anti-VCAM, anti-CD11a, anti-CD18, anti-LFA-1, anti CD54, anti-CD102, anti-CD50, anti-D29 and anti-pan cadherin. All antibodies were commercially available. Polyclonal antibody to galectin-3 (gift of Dr. Avraham Raz, Karmonas Cancer Institute, Detroit, Mich.; Inohara and Raz (1995) Cancer Res. 55:3267–3271). Radioactive tumor cells were allowed to adhere to HBME-1 cells for 30 minutes, washed to remove non-adherent cells, and assayed for gamma counts.

Figure 3:
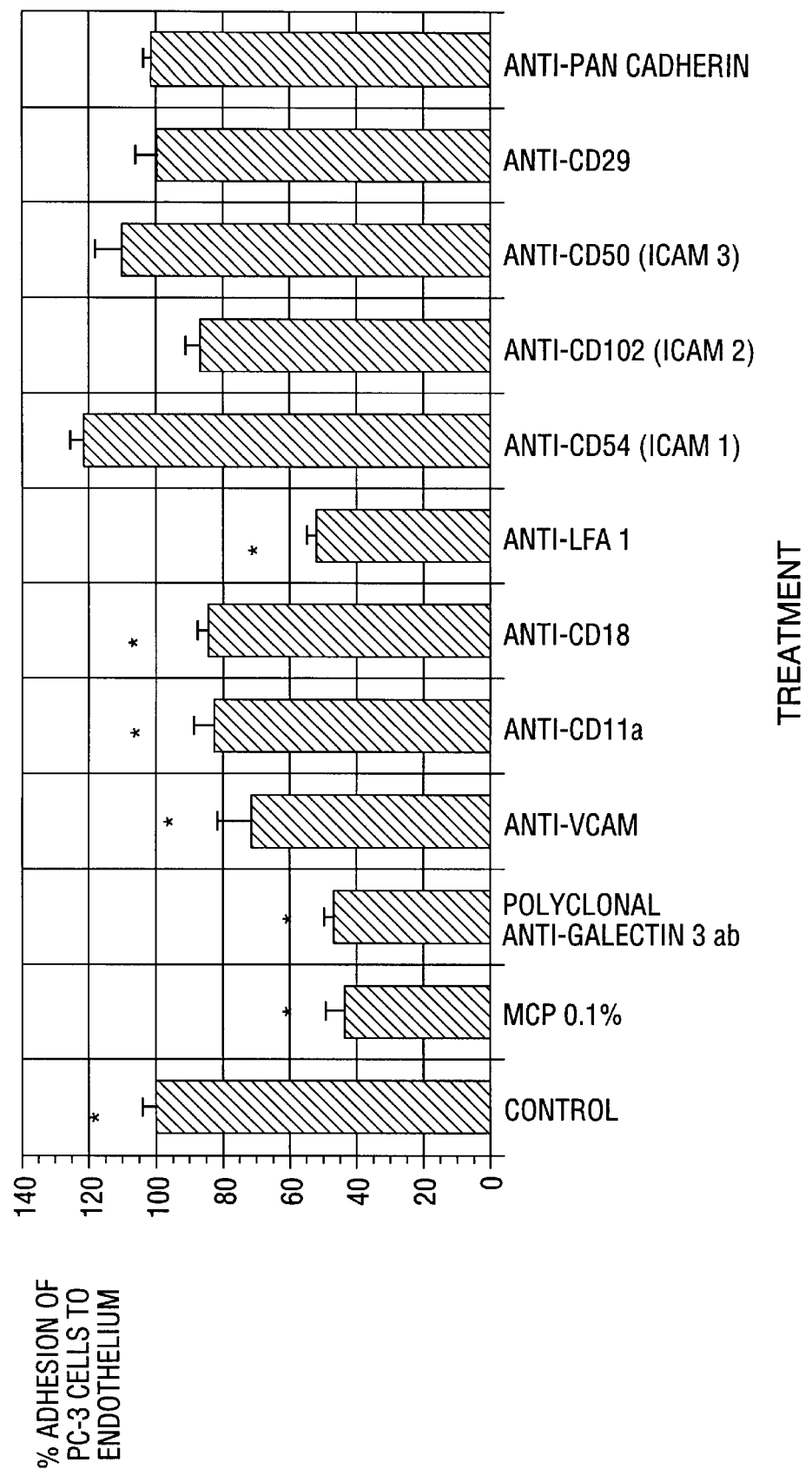
FIG. 3 is a graph showing inhibition of adhesion of PC-3 cells to immortalized HBME-1 cells using a number of antibodies.(* p<0.01).

The results of the adhesion inhibition assay are shown in FIG. 3. FIG. 3 shows that a polyclonal antibody to galectin-3, a molecule which binds galactose residues, was a strong adhesion inhibitor (FIG. 3). Adhesion of prostate cancer cells to HBME-1 cells was also inhibited in a dose dependent manner by the galactose-containing carbohydrate modified citrus pectin (approximately 50% inhibition at a pectin concentration of 0.1%) and tumor cells treated with the protein glycosylation inhibitor tunicamycin demonstrated less affinity for the endothelium (data not shown). These results suggest that carbohydrate residues are significant mediators of cell adhesion.

FIG. 3 also shows that antibodies to CD11a, CD18, LFA-1 and CD31 all inhibited binding from 20–60%. In addition, high concentrations (0.5 mM) of peptides containing RGD sequences (Matsuo et al (1994) Circulation 90:2203–2206) blocked adhesion up to 70% (data not shown). These results suggest that integrin interactions are important in maintaining adhesion between the docked tumor cell and the endothelial cell.

It is clear from the above examples that the present invention provides compositions and methods useful in the screening of anti-bone metastatic compounds. Those skilled in the art know that various changes could be made in the above examples and methods without departing from the scope of the invention. It is intended that all matter contained in the above description shall be interpreted as illustrative and not limiting.

I claim:

1. A method of testing compounds for the ability to effect binding of cancer cells to endothelial cells,
    a) providing:
        i) one or more test compounds;
        ii) cancer cells; and
        iii) immortalized human bone marrow endothelial cells capable of binding to said cancer cells;
    b) mixing said immortalized human bone marrow endothelial cells and said cancer cells under conditions such that said cancer cells and said immortalized human bone marrow endothelial cells can bind to one another, wherein said mixing is done in the presence and absence of said test compound; and
    c) comparing the extent of binding of said cancer cells and said immortalized human bone marrow endothelial cells in the presence and absence of said test compound, such that the ability of said compound to effect the binding of said cancer cells to said endothelial cells is determined.

2. The method of claim 1, wherein said cancer cells are selected from the group consisting of prostate cancer cells, lung cancer cells, colon cancer cells, and breast cancer cells.

3. The method of claim 2, wherein said cancer cells are prostate cancer cells.

4. The method of claim 1, wherein said compound is an antibody to a galectin.

5. The method of claim 1, wherein said compound is a polypeptide comprising the sequence Arg-Gly-Asp.

6. A method of screening compounds for the ability to reduce, prevent, or inhibit metastasis of cancer cells to bone marrow tissue, comprising:
    a) providing:
        i) one or more test compound;
        ii) said cancer cells; and
        iii) immortalized human bone marrow endothelial cells capable of adhesion to said cancer cells;
    b) mixing
        said immortalized human bone marrow endothelial cells with said cancer cells under conditions such that said cancer cells and said immortalized human bone marrow endothelial cells can adhere to one another, wherein said mixing is done in the presence and absence of said test compound; and
    c) detecting a reduction in adhesion of said cancer cells and said immortalized human bone marrow endothelial cells mixed in the presence of said test compound as compared to adhesion of said cancer cells and said immortalized human bone marrow endothelial cells in the absence of said test compound.

7. The method of claim 6, wherein said cancer cells are selected from the group consisting of prostate cancer cells, lung cancer cells, colon cancer cells, and breast cancer cells.

8. The method of claim 7, wherein said cancer cells are prostate cancer cells.

* * * * *